US011725002B2

(12) United States Patent
Yamada et al.

(10) Patent No.: US 11,725,002 B2
(45) Date of Patent: *Aug. 15, 2023

(54) DETECTION REAGENTS AND KIT FOR IDENTIFYING OXIDIZED STATE AND GLYCATED STATE OF LOW-DENSITY LIPOPROTEINS

(71) Applicants: FUSO PHARMACEUTICAL INDUSTRIES, LTD., Osaka (JP); Ken-ichi Yamada, Fukuoka (JP)

(72) Inventors: Ken-ichi Yamada, Fukuoka (JP); Tomomi Ide, Fukuoka (JP); Yuma Ishida, Fukuoka (JP); Go Ichien, Tokyo (JP); Keiichi Yamamoto, Osaka (JP)

(73) Assignees: Ken-ichi Yamada, Fukuoka (JP); FUSO PHARMACEUTICAL INDUSTRIES, LTD., Osaka (JP)

(*) Notice: Subject to any disclaimer, the term of this patent is extended or adjusted under 35 U.S.C. 154(b) by 176 days.

This patent is subject to a terminal disclaimer.

(21) Appl. No.: 16/609,028

(22) PCT Filed: Apr. 27, 2018

(86) PCT No.: PCT/JP2018/017287
§ 371 (c)(1),
(2) Date: Oct. 28, 2019

(87) PCT Pub. No.: WO2018/199317
PCT Pub. Date: Nov. 1, 2018

(65) Prior Publication Data
US 2020/0140426 A1 May 7, 2020

(30) Foreign Application Priority Data
Apr. 28, 2017 (JP) ................. 2017-090740

(51) Int. Cl.
G01N 21/64 (2006.01)
G01N 21/78 (2006.01)
G01N 33/533 (2006.01)
C07D 413/12 (2006.01)
C07K 16/18 (2006.01)

(52) U.S. Cl.
CPC ............ C07D 413/12 (2013.01); C07K 16/18 (2013.01); G01N 21/6428 (2013.01); G01N 21/78 (2013.01); G01N 33/533 (2013.01)

(58) Field of Classification Search
CPC .. C07D 413/12; C07K 16/18; G01N 21/6428; G01N 21/78; G01N 33/533; G01N 33/6893; G01N 33/92
See application file for complete search history.

(56) References Cited

U.S. PATENT DOCUMENTS

2014/0273055 A1 9/2014 Kerr et al.
2018/0328951 A1* 11/2018 Yamada ................ G01N 33/92

FOREIGN PATENT DOCUMENTS

| JP | 2008164554 A | 7/2008 |
|---|---|---|
| JP | 2009108037 A | 5/2009 |
| JP | 2012225762 A | 11/2012 |
| JP | 2016513795 A | 5/2016 |
| WO | 2014079946 A1 | 5/2014 |

OTHER PUBLICATIONS

EPO Extended European Search Report for Corresponding EP Appln No. 18791391.8; dated Aug. 20, 2020.
Timothy J. Lyons, MD, "Glycation and Oxidation: A role in the Pathogenesis of Atherosclerosis", The American Journal of Cardiology; vol. 71, Issue 6, Feb. 25, 1993, pp. B26-B31.
"About Glycation Stress," Karada Lab, Inc.; [online] Nov. 10, 2016, [retrieval date Jul. 19, 2018], internet< //web.archive.org/web/20161110173212/ ://ebn.arkray.co.jp/disciplines/glycation-stress/stress-01/>.
Negre-Salvayre et al., "Advanced lipid peroxidation end products in oxidative damage to proteins. Potential role in diseases and therapeutic prospects for the inhibitors", British Journal of Pharmacology; 2008; 153, pp. 6-20.
Javadzadeh et al. "Serum Paraoxonase Phenotype Distribution in Exudative Age-Related Macular Degeneration and its relationship to homocysteine and oxidized low-density lipoprotein", The Journal of Retinal and Vitreous Diseases; vol. 32, No. 4, 2012; pp. 658-666.
Cerami et al., "Glucose and Aging", Sci. Am. 256; pp. 82-88 1987.
Itabe et al., "Measurement of Plasma Oxidized Low-Density Lipoprotein and its Clinical Implications", Journal of Atherosclerosis and Thrombosis; vol. 14, No. 1, 2007; pp. 1-11.
International Preliminary Report on Patentability corresponding to Application No. PCT/JP2018/017287; dated Nov. 7, 2019.
Kotani et al., "Distribution of immunoreactive malondialdehyde-modified low-density lipoprotein in human serum", Biochimica et Biophysica Acta 1215 (1994) 121-125.
Yamada et al., "Fluorescence probes to detect lipid-derived radicals," Nature Chemical Biology; vol. 12, pp. 608-614, Dated Aug. 2016.
Saito et al., "Reductions in degree of mineralization and enzymatic collagen cross-links and increases in glycation-induced pentosidine in the femoral neck cortex in cases of femoral neck fracture", Osteoporos International.; 2006, vol. 17: pp. 986-995.

(Continued)

Primary Examiner — Shafiqul Haq
Assistant Examiner — Nam P Nguyen
(74) Attorney, Agent, or Firm — Cantor Colburn LLP

(57) ABSTRACT

A detection reagent for comprehensively detecting an oxidized state and a glycated state of a low-density lipoprotein. While an oxidized low-density lipoprotein and a glycated low-density lipoprotein are detected with a fluolophore-labelled antibody, a lipid radical is detected with a fluorescent nitroxide 2,2,6-trimethyl-4-(4-nitrobenzo[1,2,5]oxadiazol-7-ylamino)-6-pentylpiperadine-1-oxyl (NBD-Pen).

9 Claims, 4 Drawing Sheets

(56) References Cited

OTHER PUBLICATIONS

Brownlee et al., "Aminoguanidine Prevents Diabetes-Induced Arterial Wall Protein Cross-Linking", Science. 1986; 232: pp. 1629-1632.
Holvoet et al., "Association of High Coronary Heart Disease Risk Status With Circulating Oxidized LDL in the Well-Functioning Elderly", Arterioscler Thromb Vasc. Biol.; 2003, 23(8). pp. 1444-1448.
Miyata et al., "2-Isoproylidenehydrazono-4-oxo-thlazolidin5-ylacetanilide (OBP-9195) treatment inhibits the development of intimal thickening after balloon injury of rat carotid artery: role of glycoxidation and lipoxidation reactions in vascular tissue damage", FEBS Letters 445 (1999) pp. 202-206.
Reddy et al., "Involvement of Maillard Reactions in Alzheimer Disease," Neurotoxicity Research, 2002, vol. 4 (3), pp. 191-209.
International Search Report for International Application No. PCT/JP2018/017287 dated Jul. 31, 2018.
EPO Office Action for corresponding EP Application No. 18791391.8; dated Sep. 28, 2021.
Wang et al., "A reversible fluorescence probe for detection of ClO-/AA redox cycle in aqueous solution and in living cells." Elesevier; Talanta 147 (2016) pp. 468-472.
Hollyfield et al., "Oxidative damage-induced inflammation initiates age-related macular degeneration"; Nature Medicine; vol. 14, No. 2; Feb. 2008; pp. 194-198.
Maeda et al., "IKKβ Couples Hepatocyte Death to Cytokine-Driven Compensatory Proliferation that Promotes Chemical Hepatocarcinogenesis", Cell, vol. 121; Jul. 1, 2005; pp. 977-990.
Park et al., "Dietary and Genetic Obesity Promote Liver Inflammation and Tumorigenesis by Enhancing IL-6 and TNF Expression"; Cell; 140, Jan. 22, 2010; pp. 197-208.
Schutt et al., "Proteins Modified by Malondialdehyde, 4-Hydroxynonenal, or Advanced Glycation End Products in Lipofuscin of Human Retinal Pigment Epithelium;" Investigative Ophthalmology & Visual Science;, vol. 44, No. 8; Aug. 2003; pp. 3663-3668.
USPTO Non-Final Office Action for corresponding U.S. Appl. No. 15/965,096; dated Feb. 11, 2022.
Verna et al., "N-Nitrosodiethylamine Mechanistic Data and Risk Assessment: Bioactivation, DNA-Adduct Formation, Mutagenicity, and Tumor Initiation"; Pharmacol. Ther.; vol. 71, No. 1/2, 1996; pp. 57-81.

* cited by examiner

FIG. 1
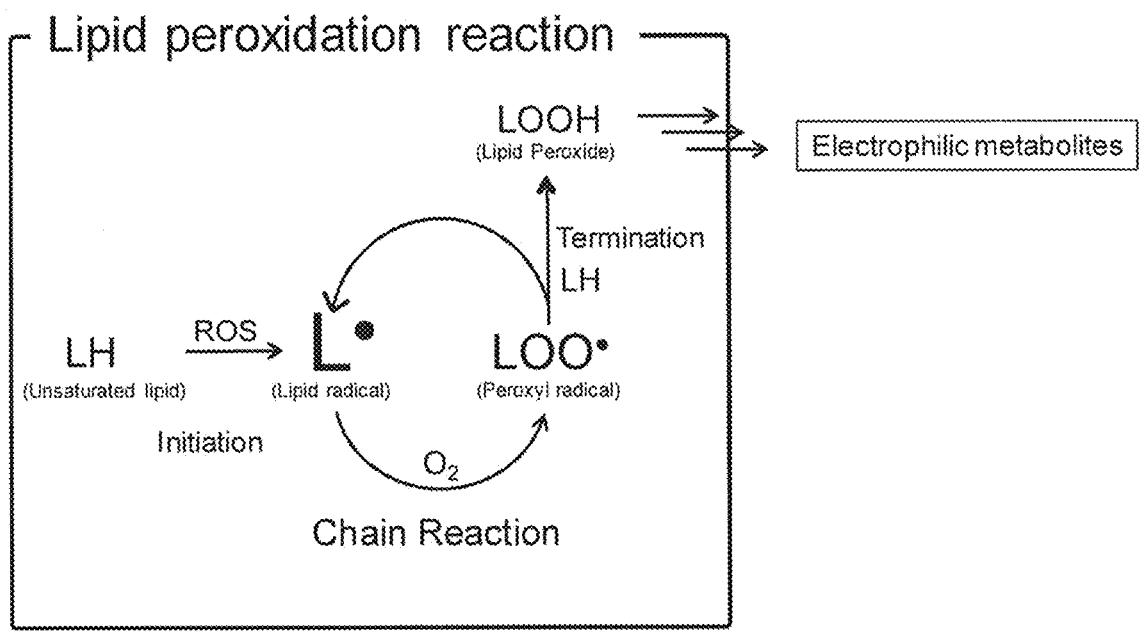
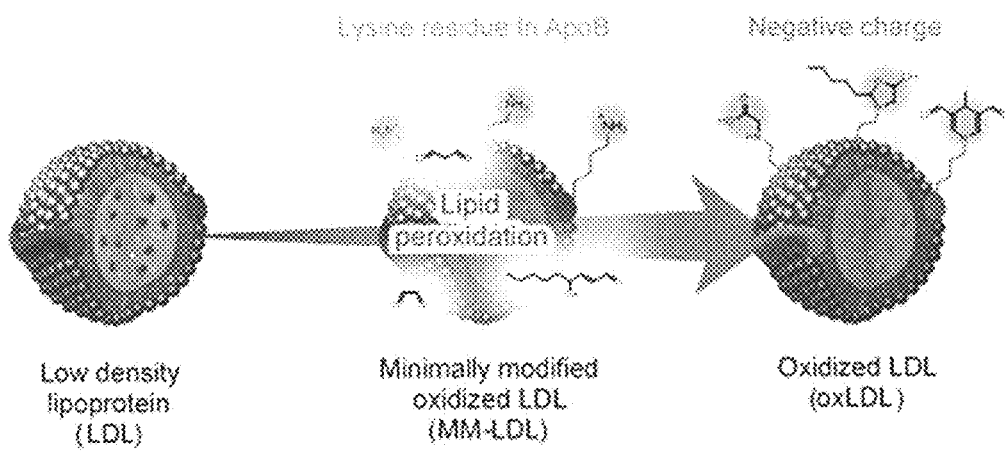
FIG. 2A          FIG. 2B          FIG. 2C (n = 3, mean + SD, v.s. Hemin: 0 µM, **p < 0.01)

NBD-Pen  Oil Red O

DETECTION REAGENTS AND KIT FOR IDENTIFYING OXIDIZED STATE AND GLYCATED STATE OF LOW-DENSITY LIPOPROTEINS

CROSS REFERENCE TO RELATED APPLICATIONS

This is the U.S. national stage of application No. PCT/JP2018/017287, filed on Apr. 27, 2018. Priority under 35 U.S.C. § 119(a) and 35 U.S.C. § 365(b) is claimed from Japanese Patent Application No. 2017-090740, filed Apr. 28, 2017; the disclosures of which are incorporated herein by reference.

TECHNICAL FIELD

The present invention relates to a technique for visually detecting oxidized and glycated lipoproteins. More specifically, the present invention provides detection reagents and kits for detecting an oxidized state of a lipid and a glycated state of a protein in a low-density lipoprotein by fluorescence observation.

BACKGROUND ART

In recent years, it has been found that oxidation and glycation of lipids promote aging. It has also become clear that lipids that have undergone modifications such as oxidation and glycation are involved in various diseases. Then, many studies have been made to elucidate a cause of such lipid modification (oxidation and glycation), which are useful not only in fields of aging prevention and beauty but also in preventing and treating diseases.

Reactive oxygen species (ROS) such as a superoxide anion radical, a hydroxyl radical, a hydrogen peroxide and a singlet oxygen affect various phenomena in living bodies. Among them, a hydroxyl radical is extremely reactive and can cause various diseases. Therefore, researches are being actively promoted. Such hydroxyl radicals are known to act on lipids to generate lipid radicals.

Since lipid radicals are highly reactive and unstable, once lipid radicals are generated, chain lipid peroxidation occurs, resulting in lipid peroxide formation, and further formation of electrophilic compounds as metabolites thereof. A lipid contains a lot of unsaturated fatty acids, and hydrogen atoms of its active methylene moiety are extracted. Therefore, they are susceptible to attack by free radicals to induce a lipid peroxidation chain reaction, which is composed of processes shown in Reaction formulas (a) to (c) (FIG. 1).

[Equation 1]

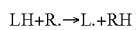  (a)

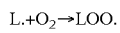  (b)

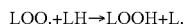  (c)

A free radical (R.) extracts a hydrogen element from an unsaturated fatty acid (LH) to initiate chain reactions (a); the generated lipid radical (L.) and an oxygen molecule react to generate a lipid peroxyl radical (LOO.) (b); and the lipid peroxyl radical subtracts a hydrogen atom from a neighboring unsaturated fatty acid to generate a lipid peroxide (LOOH) and another lipid radical (L.) (c). The regenerated lipid radical (L.) initiates a next chain reaction cycle.

Lipid peroxide (LOOH) is converted into several hundred or more electrophilic compounds including malondialdehyde, 4-hydroxy-2-nonenal, acrolein, propanal and glyoxal as its metabolites.

These metabolites alone or complexes formed with a protein are known to have cytotoxicity, inflammation, and mutagenicity, respectively.

In a living body, a water-insoluble lipid binds to an apoprotein to form a lipoprotein. Cholesterol essential for cell membrane formation is also insoluble in water and similarly binds to an apoprotein. Lipoproteins may be classified into high density lipoprotein (HDL), low-density lipoprotein (LDL) and the like according to their specific gravity.

In particular, lipids contained in LDL (FIG. 2a) generate lipid radicals by the action of ROS and the like, and metabolites are formed via lipid peroxides. A LDL in a state where only a lipid has undergone oxidative modification in this way (an oxidized-state LDL) is referred to as minimally modified oxidized LDL (MM-LDL) (FIG. 2b). Furthermore, the formed metabolite binds via lysine residues or arginine residues of the protein in LDL to form so-called oxidized LDL (OxLDL) (FIG. 2c).

As shown in FIG. 3, such oxidized LDLs are known to cause various diseases including age-related macular degeneration (AMD) and arteriosclerosis (e.g., Non-Patent Documents 1 and 2).

In addition, it has been known that when the blood sugar level rises, saccharides bind to proteins to become carbonyl compounds such as 3-deoxyglucosone (3-DG), glyoxal (GO), methylglyoxal (MGO), glyceraldehyde, and glycolaldehyde, and eventually bind to lysine residues (Lys) and arginine residues (Arg) of the protein to form advanced glycation end products (AGEs) represented by Pentosidine, Crossline, (Nε-carboxymethyl)lysine (CIVIL), (Nε-carboxyethyl)lysine (CEL), Pyrraline. It is known that accumulation of such AGEs in a living body causes various diseases. For example, it is reported that accumulation of AGEs in blood vessels causes arteriosclerosis (Non-patent document 3), that accumulation in bone causes osteoporosis (Non-patent document 4), and that accumulation in brain causes Alzheimer's disease (Non-patent document 5).

Proteins in LDL are glycated to become glycated LDLs.

As discussed above, it has been found that oxidation or glycation of lipids and proteins constituting LDL causes various diseases throughout a living body. Therefore, various countermeasures have been studied, and technologies have been developed for detecting LDL in an oxidized state (MM-LDL, OxLDL) and glycated LDL.

RELATED DOCUMENT

Non-Patent Documents

Non-Patent document 1: Javadzadeh, A. et al. Retina. 2012, 32(4), 658

Non-Patent document 2: Holvoet, P. et al. Arterioscler. Thromb. Vasc. Biol. 2003, 23(8), 1444

Non-Patent document 3: Brownlee M., et al. Science. 1986; 232: 1629-1632

Non-Patent document 4: Saito M., et al. Osteoporos Int. 2006; 17: 986-995

Non-Patent document 5: Reddy V P, et al. Neurotox Res. 2002; 4: 191-209

Non-Patent document 6: Itabe H. et al. J. Atheroscler, Thromb. 2007, 14(1), 1-11

Non-Patent document 7: Cerami A., et al., Sci. Am. 256; 90-96: 1987

Non-Patent document 8: Kotani K et al., Biochim Biophys Acta. 1215:121-5, 1994

Non-Patent document 9: Miyata T, et al., FEBS Lett 445: 202-206, 1999

DISCLOSURE OF THE INVENTION

Problem to be Solved by the Invention

Itabe et al. comprehensively considered results obtained by various immunological detections methods and confirmed that those results differed according to the respective detection methods (Non-Patent document 6). More specifically, although both the method of Itabe et al. and an MX kit provided by Kyowa Medex Co., Ltd. measure an oxidized LDL concentration by a sandwich ELISA method using a DLH3 antibody, the correlation was week (FIG. 4).

The DLH3 antibody recognizes oxidized phosphatidylcholine formed on oxidized LDLs. However, as discussed above, various complexes of proteins and metabolites of lipid peroxides (LOOH) such as malondialdehyde (MDM), 4-hydroxy-2-nonenal (HEN), acrolein (ACR), propanal, and glyoxal exist on oxidized LDLs. That is, the conventional methods observe merely a part of oxidization markers for oxidized LDLs.

Many of the AGEs on glycated LDLs are fluorescent and emit fluorescence at an excitation wavelength of 370 nm and an emission wavelength of 440 nm (e.g., Non-Patent document 7). Therefore, methods are researched for measuring fluorescence directly from human skins. Pentosidine is the only fluorescent AGE which has been confirmed to exist in skins, but detection of it has not succeeded yet.

On the other hand, antibodies recognizing Pentosidine, CIVIL, CEL, Pyrraline, and an ELISA kit for detecting AGEs are already commercially available.

Thus, although respective locations where oxidization or glycation occurred have been fluorescently measured, a method for comprehensively observing modified states (oxidized and/or glycated states) of LDLs has not been developed. Accordingly, the present inventors endeavored to provide a method for comprehensively observing modified states of LDLs.

Means for Solving the Problem

The present inventors, in a previous study, extracted lipids from a living body which had undergone oxidation stress and captured lipid radicals or radical fragments thereof by letting a fluorescent nitroxide 2,2,6-trimethyl-4-(4-nitrobenzo[1,2,5]oxadiazol-7-ylamino)-6-pentylpiperadine-1-oxyl (NBD-Pen) represented by a structural formula (1):

[Chemical Formula 1]

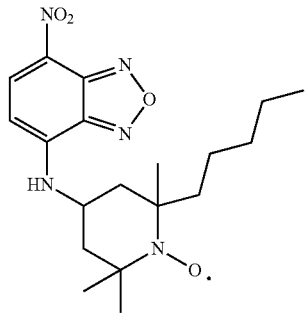

(1)

on such lipid extracts to develop a fluorescently-detecting method.

Then the present inventors succeeded in detecting modified states of LDLs individually or comprehensively by performing simultaneously or gradually detection of minimally-modified oxidized LDLs by fluorescent detection using the aforementioned fluorescent nitroxide, detection of oxidized LDLs by an ELISA method, and detection of glycated LDLs by an ELISA method, to fluorescently visualize all the oxidized and glycated states of LDLs.

When a fluorescent emission wavelength for detecting minimally-modified oxidized LDLs, a fluorescent emission wavelength for detecting oxidized LDLs, and a fluorescent emission wavelength for detecting glycated LDLs are different from each other, three kinds of modified states can be separately identified. In addition, when the fluorescence emission wavelengths thereof are similar to each other, the modification states of the LDL may be comprehensively confirmed.

Effects of the Invention

By fluorescently visualizing states of modifications (oxidation and glycation) from which LDLs suffer, useful knowledge may be obtained for early detection, diagnosis and improvement in treatment of diseases caused by modified LDLs.

BRIEF DESCRIPTION OF THE DRAWINGS

FIG. 1 A schematic diagram for the lipid peroxidation reaction.

FIG. 2 A schematic illustration showing oxidized states of a low-density lipoprotein (LDL).

MODE FOR CARRYING OUT THE INVENTION

Figure 3:
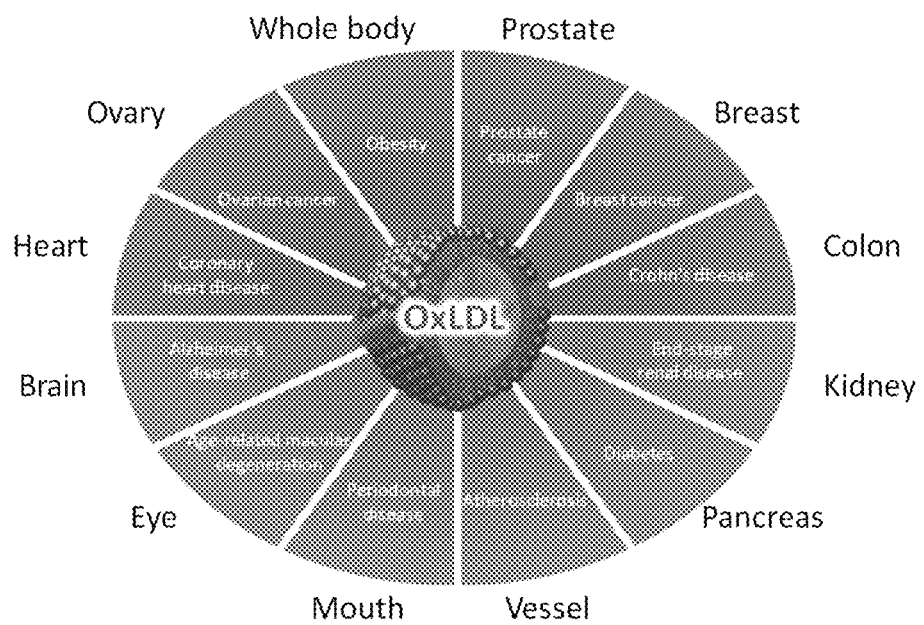
FIG. 3 Diseases related to oxidized LDLs.
Figure 4:
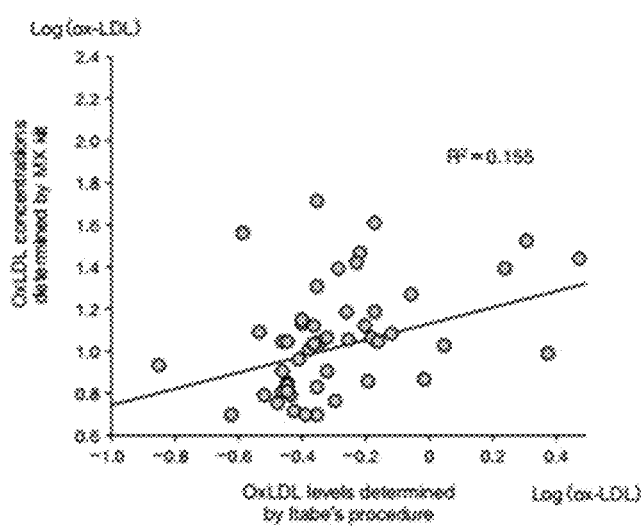
FIG. 4 A graph indicating a correlation between results from two conventional detection methods for oxidized LDLs (Source: Non-Patent document).

Reference Example 1: Development of Fluorescent Nitroxide

The present inventors have developed a novel synthesis method for the 2,6-substituted TEMPO nitroxide 2,2,6,6-tetramethylpiperadine-N-oxyl represented by the structural formula (2):

[Chemical Formula 2]

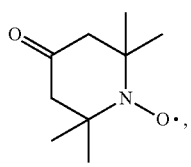

(2)

and found that when an alkyl chain is introduced around the radical, lipid affinity and an ability to suppress lipid peroxidation are improved and, then, lipid radicals can be effectively captured.

Further, a nitroxide (NO.) is a stable radical with paramagnetism and has a property of attenuating fluorescence due to photo-induced electron transfer with charge-separated states and intersystem crossing by electron-spin exchange. Therefore, a fluorescent nitroxide in which a fluorophore is covalently bound to nitroxide is in a fluorescence-quenched state due to intramolecular electron transfer. However, when a nitroxide loses paramagnetism by reacting with a free radical, electron transfer no longer occurs and a fluorescent nitroxide in a fluorescence-emitting state is formed. That is, a fluorescent nitroxide is a useful probe for detecting capture of lipid radicals by fluorescence observation.

The present inventors replaced a carbonyl group at position 4 of a TEMPO nitroxide with an amino group and covalently bound fluorescent 7-nitrobenzofurazan (NBD) represented by the structural formula (3):

[Chemical Formula 3]

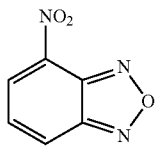

(3)

to maintain it in the vicinity of a radical site of the TEMPO nitroxide.

Most lipid molecules as detection targets exist in a living membrane and form a hydrophobic environment. Therefore, an environment-dependent fluorophore, the fluorescence of which is attenuated in a hydrophilic environment and which emits highly intense fluorescence selectively in a hydrophobic environment, is optimal. Then, the present inventors selected NBD which is widely used as a fluorophore in lipid fields such as biological membrane phase transition and membrane fusion, or intracellular lipid metabolism.

NBD derivatives have an excitation wavelength of about 470 nm, being suitable for argon laser excitation (488 nm), and are very advantageous because they can be applied to imaging by use of a fluorescence microscope.

Furthermore, it is also advantageous to use NBD derivatives from the viewpoint of having an emission maximum of about 530 nm and reducing autofluorescence due to biological substances.

The present inventors have found that when an alkyl chain is introduced in the vicinity of a radical site of the TEMPO nitroxide, lipid affinity and steric hindrance of the compound change. As a result, lipid radicals can be effectively captured.

As a NBD-nitroxide with high lipid reactivity, the inventors synthesized Compound A (NBD-Pen):

[Chemical Formula 4]

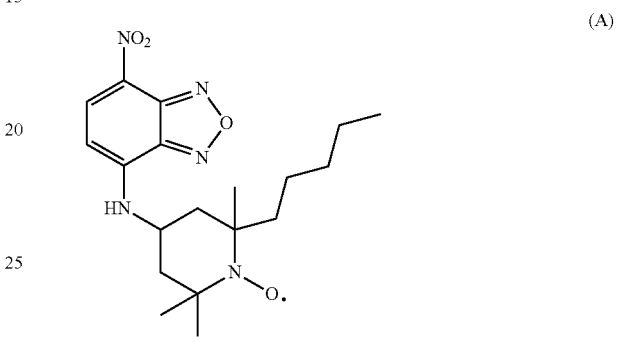

(A)

which has two methyl groups at position 2; and a methyl group and a pentyl group at position 6 as substituents.

Example 1: Detection of Lipid Radicals in LDL with NBD-Pen

First, the present inventors confirmed whether Compound A (NBD-Pen) could detect lipid radicals existing in LDL. For oxidative stimulation, the iron porphyrin Hemin:

[Chemical Formula 5]

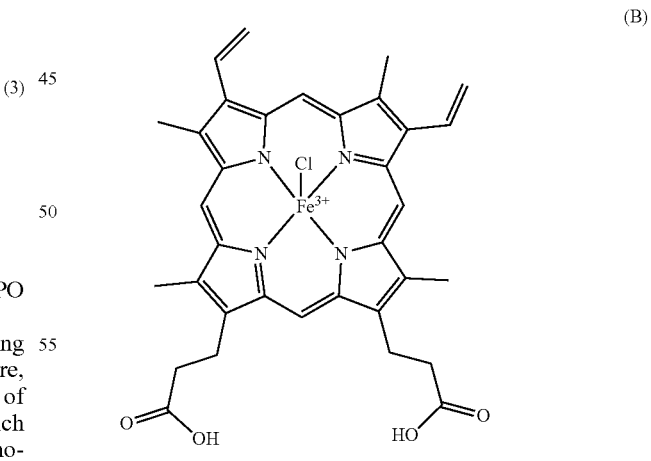

(B)

was used. Its affinity to copper ions, iron ions and LDL is high and it is pointed out that it is involved in arteriosclerosis.

To a solution of 20 µg protein/ml of LDL and 10 µM of NBD-Pen in phosphate buffered saline (PBS) containing 0.5% of MeCN were added 0-3 µM of $CuSO_4$, $FeSO_4$ or Hemin, to generate lipid radicals.

Figure 5:
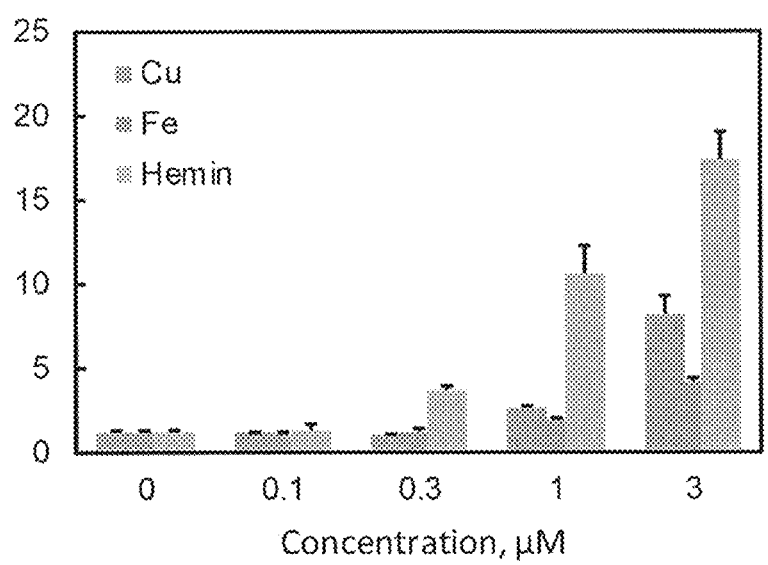
FIG. 5 A graph comparing sensitivities of detection for lipid radicals in LDLs by NBD-Pen with different radical generators.

After incubation for 60 minutes at 37° C., fluorescence intensities ($\lambda_{ex}$: 470 nm, $\lambda_{em}$: 530 nm) of these solutions were measured at 37° C., it was found that the fluorescence intensities increased in a concentration-dependent manner with either $Cu^{2+}$, $Fe^{2+}$ or Hemin; and that Hemin addition in particular showed high sensitivity of fluorescence detection (FIG. 5). This result suggested that NBD-Pen reacts with lipid radicals generated in LDL.

Example 2: Comparison Between the Detection Method Using NBD-Pen According to the Present Invention and Conventional Methods Against Oxidized LDLs There are mainly two detection methods currently used in detecting oxidized LDLs.

The first is agarose gel electrophoresis. LDLs which have undergone oxidative denaturation have an increased negative charge due to protein modification. Therefore, when a potential gradient is applied after injecting a sample into an agarose gel, electric mobility of negative LDLs to the positive side increases. That is, the oxidation degree of LDL can be measured by this electric mobility. However, since the oxidized LDL concentration in human blood is as low as 0.1% or less the LDL concentration, it is very difficult to detect oxidized LDLs in blood with the sensitivity of this method.

The second is an ELISA method using a monoclonal antibody against oxidized LDLs. The ELISA method can detect with high sensitivity due to the use of an antibody, and detection of blood oxidized LDL actually succeeded. Therefore, research on oxidized LDLs progressed rapidly. However, since LDLs are huge particles consisting of lipids and proteins, an anti-oxidized LDL monoclonal antibody consequently recognizes only a part of the particle but not the whole. Therefore, many ELISA measurements employ a sandwich ELISA method using a combination of an antibody recognizing oxidation-modified parts and an antibody recognizing ApoB proteins in LDLs in order to detect oxidized LDLs. In addition, lipid peroxidation metabolites which are generated during a LDL oxidation process take a variety of chemical structures, and since there are a wide variety of modified protein sites, it is necessary to prepare antibodies corresponding to the respective sites. Therefore, many types of anti-oxidized LDL antibodies have been developed. For example, ML25 (Non-Patent document 8), NA59 (Non-Patent document 9), an anti-Acrolein monoclonal antibody (e.g., Japan Institute for the Control of Aging, NIKKEN SEIL CO., Ltd., MAR) and the like, which recognize MDA-Lys, HNE-Lys, or Acrolein-Lys formed by the modification of lysine residues (Lys) with lipid peroxidation metabolites MDA or HNE, are known.

As discussed above, conventional agarose gel electrophoresis and ELISA methods target only oxidized LDLs after protein modification. On the other hand, detection methods for oxidized lipids include a measurement of the 230 nm absorption band due to formation of conjugated dienes during lipid oxidation, LC/MS, a TBARs (2-thiobarbituric acid reactive substances) method and the like. Detection by absorbance spectrophotometry is a useful tool for understanding the details of LDL oxidation mechanisms because it can track a lipid oxidation reaction over time. However, it is insufficient in terms of sensitivity and selectivity. In contrast, LC/MS and a TBARs method which detects MDA are highly sensitive. However, since the former lacks versatility because of requiring an expensive apparatus and long measurement times per sample, and the latter changes unoxidized lipids to MDL-like structures when heat-treated during adduct formation, there is room for improvement.

The absorption band around 234 nm of conjugated dienes formed during lipid oxidation was tracked by absorbance spectrophotometry. In addition, a measurement was performed by use of diphenyl-1-pyrenylphosphate (DPPP), which is a lipid peroxide (LOOH) detection fluorescent probe. As a result, in the concentration range used in this example, neither method could detect lipid peroxides (data not shown).

Next, similarly to Example 1, LDLs that had undergone 60 minutes oxidation stimulation by Hemin addition were evaluated by electrophoresis and a TBARs method.

Specifically, to a solution of 20 μg protein/ml of LDL and 10 μM of NBD-Pen in phosphate buffered saline (PBS; pH 7.4) containing 0.5% of MeCN were added 0-3 μM of Hemin, to generate lipid radicals. After incubation for 60 minutes at 37° C., these reacted solutions were investigated by the respective methods.

[Measurement of LDL Electric Mobility by Electrophoresis]

A solution obtained by mixing 20 μg protein/ml LDL and 0-3 μM of Hemin in PBS (pH 7.4) and they were allowed to react for one hour was added to agarose gel at 10 μl and was electrophoresed at a voltage of 50 V for two hours. Agarose gel was prepared by adding 1% Agarose H14 TAKARA to a TAE buffer, heating and solubilizing, then followed by pouring it into a mold and leaving the mold in a stationary state. A TAF buffer was used as an electrophoresis buffer. After staining with Coomassie Brilliant Blue (CBB), imaging was performed by use of a gel imaging apparatus to calculate electric mobility. Numerical values were expressed as ratios based on the results without addition of Hemin.

[Detection of TBARs in LDL by a TBARs Method]

To 160 μl of a solution obtained by mixing 20 μg protein/ml LDL and 0-3 μM of Hemin in PBS (pH 7.4) and letting them react for one hour were added 20% acetic acid 40 μl, 1.3% thiobarbituric acid (TBA) 60 μl and 10% SDS 15 μl, and they were allowed to react at 60° C. for 40 minutes in the dark to form a MDA-TBA$_2$ adduct. After centrifugation at 2000 rpm for 4 minutes, fluorescence intensity ($\lambda_{ex}$: 532 nm, $\lambda_{em}$: 585 nm) was measured. Numerical values were expressed as ratios based on the results without addition of Hemin.

[Fluorescence Detection of Lipid Radicals in LDL by Usage of NBD-Pen]

For fluorescence detection using NBD-Pen according to the present invention, the fluorescence intensities obtained in Example 1 were expressed as ratios based on the results without addition of Hemin.

[Results]

Figure 6:
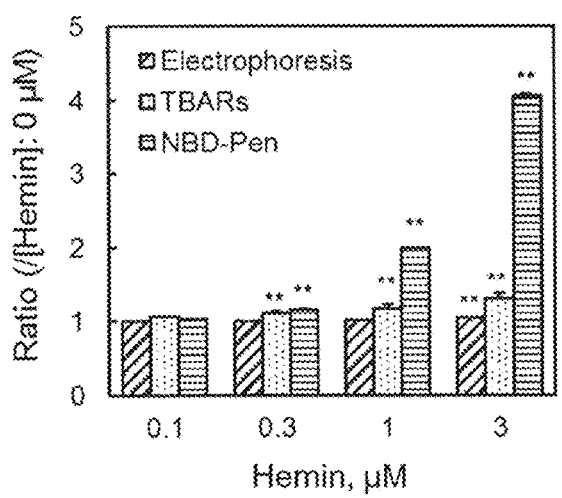
FIG. 6 A graph comparing sensitivities of the detection method using NBD-Pen according to the present invention and the conventional methods against oxidized LDLs.

Electrophoresis showed only slight movement to the negative side at 3 μM addition. The TBARs method showed that TBARs levels increased in a Hemin concentration-dependent manner, but the extent was low compared to NBD-Pen (FIG. 6).

According to the findings from Examples 1 and 2, it was confirmed that fluorescence observation of the state of oxidized LDLs could be performed effectively by oxidation stimulation with addition of Hemin and use of NBD-Pen.

Example 3: Fluorescence Mapping of Lipid Oxide Using NBD-Pen According to the Present Invention A 6-week-old male Apo-E knockout mouse (Apo−/−) was fed with a high fat diet, and 3 weeks later, NBD-Pen was administered at 500 μM/kg by intraperitoneal injection.

Figure 7A:
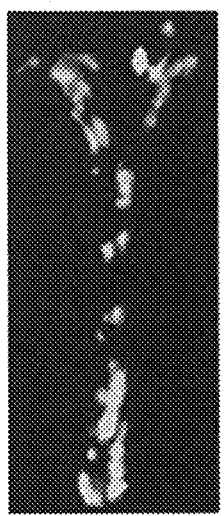
FIG. 7 Fluorescent microscopic image of an aortic sample from an arteriosclerosis model mouse administered with NBD-Pen (a); a digital image of an oil-red stained plaque (b).
Figure 7B:
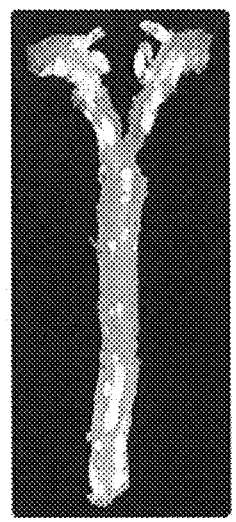

Fifteen minutes after NBD-Pen administration, the mouse was subjected to three types of mixed anesthesia and sacrificed, and the thoracic aorta was immediately removed. The excised aorta sample was observed for fluorescence derived from NBD-Pen with an excitation wavelength (470 nm) and an emission wavelength (530 nm) with a fluorescence microscope (FIG. 7a). An oil red stained image of plaques of the same aortic sample was taken with a digital camera (FIG. 7b).

The green-colored areas (shown in white in the figure), indicating fluorescence emission derived from NBD-Pen, and the orange-colored areas (shown in white in the figure), indicating oil-red stained plaques, were completely matched. This finding suggests that lipid oxides were present in plaques formed due to arteriosclerosis. That is, it was confirmed that the fluorescence method using NBD-Pen according to the present invention can detect locations of arteriosclerosis.

Example 4: Detection of Modified LDLs with NBD-Pen According to the Present Invention and an Antibody Cocktail (1) Preparation of a Kit for Detecting MM-LDL Detection of MM-LDL is performed by a fluorescence method using NBD-Pen. NBD-Pen is added to whole blood collected from a subject animal so that the final concentration becomes 50 µM, and it is reacted at 37° C. for one hour. After that, the reaction is quenched by adding 100 µM Trolox and it is centrifuged. It is isolated from the plasma obtained from the supernatant by ultracentrifugation and its fluorescence intensity ($\lambda_{ex}$: 470 nm, $\lambda_{em}$: 530 nm) is measured.

(2) Preparation of a Kit for Detecting OxLDL

Detection of oxidized LDL is performed by an enzyme-linked immunosorbent assay (ELISA) method using a mixture of primary antibodies (Antibody cocktail) against malondialdehyde (MDA), 4-hydroxy-2-nonenal (HNE) and acrolein (ACR), which are representative of lipid peroxidation metabolites derived from lipid radicals. These primary antibodies are derived from the same animal other than the animal from which the oxidized LDL of the detection subject is derived.

The present invention requires the use of a mixture of monoclonal antibodies against each of the metabolites, rather than the use of polyclonal antibodies against oxidized LDL.

For example, in the case where MDA-Lys or HNE-Lys of oxidized LDL derived from a human is detected, an antibody derived from a mouse (e.g., ML25, NA59) may be used. A secondary antibody which specifically binds to this primary antibody is used. As such secondary antibodies, anti-mouse antibodies derived from animals other than humans and mice, such as rabbit anti-mouse IgG, can be used.

Additionally, the present invention applies a sandwich ELISA method in which the oxidized LDL is sandwiched between a capture antibody for immobilizing oxidized LDL on a microplate and a primary antibody that detects lipid peroxidation metabolites on the oxidized LDL; and an indirect method in which a secondary antibody labeled with a label molecule is reacted against the primary antibody.

The secondary antibody is labelled with a label molecule to be detected by an optical method.

A secondary antibody labelled with an enzyme such as horseradish peroxidase (HRP) or alkali phosphatase (ALP) may be used. When a HRP-labelled antibody is used, a chromogenic substrate such as tetramethylbenzidine (TMB), o-phenylenediamine (OPD), 2,2-azinobis[3-ethylbenzothiazoline-6-sulfonic acid] (ABTS) is added. HRP can be spectroscopically observed by oxidizing these chromogenic substrates using hydrogen peroxide as an oxidizing agent to develop strong light. When an ALP-labelled antibody is used, a chromogenic substrate such as p-nitrophenylphosphate (pNPP) is added. ALP can be spectroscopically observed by forming strong yellow p-nitrophenol from pNNP under alkaline conditions.

The secondary antibody may be labelled with any fluorescent dye. Different fluorescent dyes may be attached to respective detection subjects. However, for an oxidized state of LDL to be comprehensively visualized, it is preferable to attach a fluorescent dye common to those detection subjects.

For example, an antibody labelling kit provided by Thermo Fisher Scientific Inc. is used to fluorescently label a subject secondary antibody. Since the labelling kit includes a plurality of types of amine-reactive fluorescent dyes having different excitation wavelength/emission wavelengths, they can be appropriately selected according to the purpose of visualization.

A secondary antibody is labelled with these fluorescent dyes according to the fluorescent labeling protocol of the company. That is, fluorescent labelling is performed by using the following steps. After fluorescent labelling, purification is performed.

1.1 A 1 M solution of sodium bicarbonate is prepared by adding 1 mL of deionized water ($dH_2O$) into a vial containing sodium bicarbonate (Component B). Dissolving is performed thoroughly by vortexing or pipetting up and down the liquid. The bicarbonate solution has a pH of 8-9 and it can be stored at 2-8° C. over 2 weeks at most.

1.2 When the antibody to be labelled has a concentration of 1 mg/mL or higher in an appropriate buffer, it is diluted to 1 mg/mL and one tenth volume of a 1 M sodium bicarbonate solution (prepared in Step 1.1) is added.

When a protein is in a form of lyophilized powder from an appropriate buffer, 1 mg/mL of an antibody solution is prepared by pouring an appropriate amount of 0.1 M sodium bicarbonate buffer solution to the protein. The 1 M solution is diluted 10-fold with $dH_2O$ to prepare a 0.1M sodium bicarbonate solution.

Note: Since succinimidyl ester and TFP ester react efficiently at alkaline pH, bicarbonate is added to raise the pH of the reaction mixture (pH 8-9).

1.3 The 100 µL of protein solution (from Step 1.2) is transferred to a vial containing a reactive dye. The vial is capped and is gently inverted several times to completely dissolve the dye. Vigorously stirring the protein solution can result in protein denaturation.

Note: In order to visually confirm that the dye is thoroughly dissolved, a vial label of the reactive dye may be removed.

1.4 The solution is incubated at a room temperature for one hour. Every 10 to 15 minutes, a vial is gently inverted to mix the two reactants for enhancing the labeling efficiency.

Sensitization can also be achieved by binding biotin onto the secondary antibody and adding a fluorescently labelled avidin.

If an ELISA kit adequate for detection of oxidized LDL is not commercially available, it can be self-made.

(3) Preparation of a Kit for Detecting Glycated LDL

Detection of glycated LDLs is performed by an enzyme-linked immunosorbent assay (ELISA) using a mixture of primary antibodies (Antibody cocktail) against Pentosidin, Crossline, CIVIL, CEL, Pyrraline representing AGE. These primary antibodies are derived from the same animal other than the animal from which the glycated LDL of the detection subject is derived.

The present invention requires the use of a mixture of monoclonal antibodies against each of the metabolites, rather than the use of polyclonal antibodies against glycated LDL.

For example, in the case where CML of glycated LDL derived from a human is detected, an anti-CML antibody derived from a mouse (e.g., Cosmo Bio Co., Ltd., AGE-M01) may be used. A secondary antibody which specifically binds to this primary antibody is used. As such secondary antibodies, anti-mouse antibodies derived from animals other than humans and mice, such as rabbit anti-mouse IgG, can be used.

The secondary antibody is labelled with a label molecule to be detected by an optical method. A secondary antibody labelled with an enzyme such as horseradish peroxidase (HRP) or alkali phosphatase (ALP) may be used.

When a HRP-labelled antibody is used, a chromogenic substrate such as tetramethylbenzidine (TMB), o-phenylenediamine (OPD), 2,2-azinobis[3-ethylbenzothiazoline-6-sulfonic acid] (ABTS) is added. HRP can be spectroscopically observed by oxidizing these chromogenic substrates using hydrogen peroxide as an oxidizing agent to develop strong light.

When an ALP-labelled antibody is used, a chromogenic substrate such as p-nitrophenylphosphate (pNPP) is added. ALP can be spectroscopically observed by forming strong yellow p-nitrophenol from pNNP under alkaline conditions.

Similarly to the above explanation for the oxidized LDL, the secondary antibody may be labelled with any fluorescent dye. Different fluorescent dyes may be attached to respective detection subjects. However, for an oxidized state of LDL to be comprehensively visualized, it is preferable to attach a fluorescent dye common to those detection subjects.

Sensitization can also be achieved by binding biotin onto the secondary antibody and adding a fluorescently labelled avidin.

Similarly to the above explanation for the oxidized LDL, if an ELISA kit adequate for detection of glycated LDL is not commercially available, it can be self-made.

(4) Fluorescence Observation of Modified LDL

A 96-well microplate on which a capture antibody capturing the subject modified LDL is immobilized is prepared. If a microplate adequate for capturing the modified LDL is not available, a microplate on which a capture antibody is immobilized is obtained by dripping onto respective wells 0.2 mL of a solution (0.2 to 100 μg/mL) in which an adequate capture antibody is diluted in a carbonic acid-carbonated water buffer of PBS, incubating it at 37° C. for one hour and, then, removing the solution and cleaning the plate with a cleaning buffer three times.

A calibrator is diluted to prepare a ½ dilution series (2000, 1000, 500, 250, 125, 62.5, and 31.2 pg/mL).

A sample is prepared.

Seven wells are assigned for diluted calibrators and one well for blank.

To each well, 100 μL of diluted calibrators, blank and samples are added and it is covered with a plate sealer, and incubated at 37° C. for two hours.

The solutions in the respective wells are removed without cleaning at this time.

To each well, 100 μL of detection reagent A containing a mouse-derived primary detection antibody for oxidized LDLs (Antibody cocktail for recognizing MDA-Lys, HNE-Lys, and Acrolein-Lys), a mouse-derived primary detection antibody for glycated LDLs (Antibody cocktail for recognizing MDA-Lys, HNE-Lys, Acrolein-Lys), a mouse-derived primary detection antibody for Pentosidin, Crossline, CML, CEL, and Pyrraline, and NDB-Pen is added and it is covered with a plate sealer, and incubated at 37° C. for two hours.

As a mouse-derived primary detection antibody for oxidized LDLs, Antibody cocktail containing a mixture of ML25 or 4C7 (ab17354) (Abeam PLC), NA59 or HNEJ-2 (ab48506) (Abeam PLC), and MAR may be used.

As a mouse-derived primary detection antibody for glycated LDLs, Antibody cocktail containing a mixture of ES12 (Exocell Inc.), CML26 (ab125145) (Abeam PLC), and ab23722 (Abeam PLC) may be used.

From each well, solutions are removed in vacuo, cleaned with 350 μL of a cleaning solution, allowed for 1 to 2 minutes, after that, an operation for thoroughly removing remaining liquids from all the wells is repeated three times.

To each well, 100 μL of detection reagent B containing a secondary detection antibody is added and it is covered with a plate sealer, and incubated at 37° C. for one hour. This secondary detection antibody is a rabbit anti-mouse antibody commonly recognizing a mouse-derived primary detection antibody for oxidized LDL and a mouse-derived primary detection antibody for glycated LDL, and to which a fluorophore is bound.

As such a fluorophore, Alexa Fluor® 488 (Thermo Fisher Scientific Inc.) and the like is preferred, which is excited at 485 nm, being an excitation wavelength of NBD-Pen, and has an emission maximum at 519 nm. More preferably, NBD-NHS represented by the chemical structure (5):

[Chemical Formula 6]

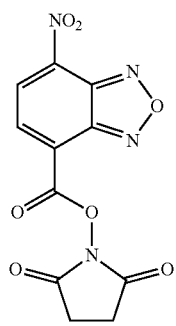

(5)

in which N-hydroxysuccinimide active ester is introduced into 7-nitrobenzofurazan (NBD) is used to fluorescently label the secondary detection antibody with NBD.

Alternatively, a fluorescent nitroxide in which a fluorophore used for the secondary antibody is bound to alkynated or azido TEMPO nitroxide represented by the chemical formula (6):

[Chemical Formula 7]

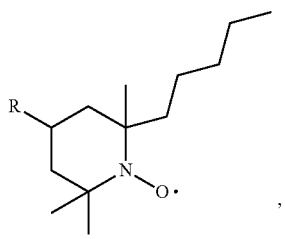

(6)

wherein R indicates an alkyne group or azido group, may also be used.

From each well, solutions are removed in vacuo, cleaned with a 350 μL of cleaning solution, allowed for 1 to 2 minutes, after that, an operation for thoroughly removing remaining liquids from all the wells is repeated three times.

To each well, 50 μL of a quenching liquid is added.

A microplate reader is used to excite the fluorophore with an excitation wavelength at 485 nm and to observe fluorescent intensity at 528 nm.

INDUSTRIAL APPLICABILITY

The fluorescent detection method according to the present invention is used to comprehensively observe modified states (oxidized and glycated states) of a low-density lipoprotein (LDL). The comprehensive observation results enhance studies on correlation between modified LDL and diseases and they can be utilized for prevention and treatment of such diseases.

The invention claimed is:

1. A detection reagent containing
    a primary detection antibody recognizing an oxidized low-density lipoprotein,
    a primary detection antibody recognizing a glycated low-density lipoprotein,
    a secondary antibody recognizing the primary detection antibody recognizing the oxidized low-density lipoprotein,
    a secondary antibody recognizing the primary detection antibody recognizing the glycated low-density lipoprotein,
    wherein the secondary antibody recognizing the primary detection antibody recognizing the oxidized low-density lipoprotein and the secondary antibody recognizing the primary detection antibody recognizing glycated low-density lipoprotein are fluorescently labelled with fluorophores, and a fluorescent nitroxide represented by the chemical structure (1):

[Chemical Formula 1]

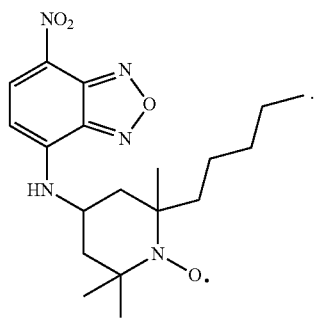

(1)

2. The detection reagent according to claim 1, wherein the primary detection antibody recognizing the oxidized low-density lipoprotein is a mixture containing at least an antibody recognizing malondialdehyde lysine, an antibody recognizing 4-hydroxy-2-nonenal lysine, and an antibody recognizing acrolein lysine.

3. The detection reagent according to claim 1, wherein the primary detection antibody recognizing the glycated low-density lipoprotein is a mixture containing at least an antibody recognizing pentosidin, an antibody recognizing crossline, an antibody recognizing (Nε-carboxymethyl)lysine, an antibody recognizing (Nε-carboxyethyl)lysine, and an antibody recognizing pyrraline.

4. A kit for identifying an oxidized state and a glycated state of a low-density lipoprotein, which includes
    a microplate on which an antibody recognizing a low-density lipoprotein is immobilized, and
    the detection reagent according to claim 1.

5. The kit according to claim 4, wherein at least one of the fluorophores is a 7-nitrobenzofurazan derivative.

6. The kit according to claim 4, wherein the fluorophores have emission wavelengths different from each other.

7. The kit according to claim 4, wherein the secondary antibody recognizing the primary detection antibody recognizing the oxidized low-density lipoprotein and the secondary antibody recognizing the primary detection antibody recognizing the glycated low-density lipoprotein are each fluorescently labelled with a fluorophore which is excited with an excitation wavelength of 485 nm and observed fluorescent intensity at 528 nm.

8. The detection reagent according to claim 1, wherein the fluorophores have emission wavelengths different from each other.

9. The detection reagent according to claim 1, wherein the secondary antibody recognizing the primary detection antibody recognizing the oxidized low-density lipoprotein and the secondary antibody recognizing the primary detection antibody recognizing the glycated low-density lipoprotein are each fluorescently labelled with a fluorophore which can be excited with an excitation wavelength at 485 nm and observed fluorescent intensity at 528 nm.

* * * * *